US012746070B2

(12) United States Patent
Demanget et al.

(10) Patent No.: US 12,746,070 B2
(45) Date of Patent: Sep. 29, 2026

(54) SURGICAL INSTRUMENT ADAPTER AND METHODS FOR NAVIGATED ORTHOPAEDIC SURGICAL PROCEDURES

(71) Applicant: DEPUY IRELAND UNLIMITED COMPANY, Ringaskiddy (IE)

(72) Inventors: Nicolas Demanget, Cambridge, MA (US); Joseph G. Wyss, Fort Wayne, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 210 days.

(21) Appl. No.: 18/604,153

(22) Filed: Mar. 13, 2024

(65) Prior Publication Data

US 2024/0341858 A1 Oct. 17, 2024

Related U.S. Application Data

(60) Provisional application No. 63/459,571, filed on Apr. 14, 2023.

(51) Int. Cl.

| | |
|---|---|
| ***A61B 34/20*** | (2016.01) |
| ***A61B 17/15*** | (2006.01) |
| ***A61B 17/17*** | (2006.01) |
| ***A61F 2/38*** | (2006.01) |

(52) U.S. Cl.

CPC ............ *A61B 34/20* (2016.02); *A61B 17/157* (2013.01); *A61B 17/1764* (2013.01); *A61F 2/3859* (2013.01)

(58) Field of Classification Search

CPC ... A61B 34/20; A61B 17/157; A61B 17/1764; A61F 2/3859

See application file for complete search history.

(56) References Cited

U.S. PATENT DOCUMENTS

| | | | | |
|---|---|---|---|---|
| 6,551,325 | B2 | 4/2003 | Neubauer et al. | |
| 7,993,341 | B2 | 8/2011 | Grimm et al. | |
| 2002/0068942 | A1 * | 6/2002 | Neubauer | A61B 17/154 606/88 |
| 2005/0209598 | A1 * | 9/2005 | Grimm | A61B 17/155 606/86 R |
| 2021/0322032 | A1 * | 10/2021 | Gogarty | A61B 34/20 |

* cited by examiner

*Primary Examiner* — Kevin T Truong
*Assistant Examiner* — Diana Jones
(74) *Attorney, Agent, or Firm* — Barnes & Thornburg LLP

(57) ABSTRACT

Systems and methods for an orthopaedic surgical procedure include a surgical instrument adapter having an elongated body with a slot define in one end and a lug positioned on the other end. The slot is sized to receive the pointer end of a navigated pointer instrument such that the pointer end is held in a predetermined position relative to the surgical instrument adapter. A method for performing the orthopaedic surgical procedure includes inserting the pointer end of the navigated pointer instrument into the slot of the adapter, inserting the lug of the adapter into a hole defined in a surgical guide instrument, positioning the surgical guide instrument on a surgically prepared surface of a patient's bone, and determining a position of the navigated pointer instrument using a surgical navigation system. By way of example, the surgical guide instrument may be a femoral finishing block or a tibial template.

17 Claims, 12 Drawing Sheets

SURGICAL INSTRUMENT ADAPTER AND METHODS FOR NAVIGATED ORTHOPAEDIC SURGICAL PROCEDURES

CROSS-REFERENCE TO RELATED CASES

This applications claims the benefit of U.S. Provisional Patent Application No. 63/459,571, filed Apr. 14, 2023, the entire disclosure of which is incorporated herein by reference.

TECHNICAL FIELD

The present disclosure relates generally to orthopaedic surgical instruments and, more particularly, to surgical navigation systems and methods for orthopaedic surgical procedures.

BACKGROUND

Joint arthroplasty is a well-known surgical procedure by which a diseased and/or damaged natural joint is replaced by a prosthetic joint, which may include one or more orthopaedic implants. To facilitate the replacement of the natural joint with the prosthetic joint, orthopaedic surgeons may use a variety of orthopaedic surgical instruments such as, for example, surgical saws, cutting guides, reamers, broaches, drill guides, drills, positioners, insertion tools and/or other surgical instruments. A surgeon may use manual instruments such as cutting blocks or other cutting guides to perform the various resections in an orthopaedic procedure. Alternatively, or in addition, a surgeon may use a computer-assisted surgical navigation system, such as a robotic-assisted surgical system, to perform the various resections in an orthopaedic procedure.

SUMMARY

According to one aspect, a surgical instrument for an orthopaedic surgical procedure may comprise an elongated body extending from a first end to a second end. The elongated body may comprise (i) an end wall positioned at the first end of the elongated body and (ii) an inner wall extending inwardly from an opening defined in the second end of the elongated body to the end wall. The inner wall and the end wall may define a slot sized to receive a pointer end of a navigated pointer instrument such that the pointer end is held in a predetermined position relative to the surgical instrument. The surgical instrument may further comprise a lug positioned at the first end of the elongated body.

In some embodiments, the lug may comprise an outer surface extending outward from the elongated body at the first end. In some embodiments, the outer surface may be cylindrical. In some embodiments, the outer surface may be tapered. In some embodiments, the outer surface of the lug may be sized to be received in a hole defined in another surgical instrument. In some embodiments, a port may be defined in the end wall, the port having a width smaller than a width of the opening defined in the second end. In some embodiments, the elongated body may comprise a scalloped cutout surface between the first end and the second end and a plurality of ridges extending from the scalloped cutout surface. In some embodiments, the slot may extend from the second end toward the first end, and the lug may extend from the first end in line with the slot. In some embodiments, an inner diameter of the slot may be sized to match an outer diameter of the pointer end. In some embodiments, the pointer end may be free to rotate relative to the surgical instrument while being held in the predetermined position relative to the surgical instrument.

According to another aspect, a method for performing an orthopaedic surgical procedure may comprise inserting a pointer end of a navigated pointer instrument into a slot defined in an adapter instrument such that the pointer end is held in a predetermined position relative to the adapter instrument. The method may further comprise inserting a lug of the adapter instrument into a hole defined in a surgical guide instrument such that the adapter instrument is held in a predetermined position relative to the surgical guide instrument. The method may further comprise positioning a first bone-contacting surface of the surgical guide instrument on a first surgically prepared surface of a patient's bone after inserting the pointer end of the navigated pointer instrument into the slot and inserting the lug into the hole. The method may further comprise determining a position of the surgical guide instrument relative to the patient's bone by sensing a position of the navigated pointer instrument using a surgical navigation system while the surgical guide instrument is positioned on the patient's bone.

In some embodiments of the method, the adapter instrument may be any of the surgical instrument adapters described herein. In some embodiments, the hole defined in the surgical guide instrument may extend between an opening defined in the first bone-contacting surface and an opening defined in an outer surface of the surgical guide instrument. In some embodiments, the surgical guide instrument may comprise a femoral finishing block and the first surgically prepared surface of the patient's bone comprises a distal cut surface of a femur. In some embodiments, the method may further comprise positioning a second bone-contacting surface of the surgical guide instrument on a posterior cut surface of the femur while the first bone-contacting surface of the surgical guide instrument is positioned on the distal cut surface of the femur. In some embodiments, the surgical guide instrument may comprise a tibial template and the first surgically prepared surface of the patient's bone comprises a transverse cut surface of a tibia. In some embodiments, the method may further comprise positioning a second bone-contacting surface of the surgical guide instrument on a sagittal cut surface of the tibia while the first bone-contacting surface of the surgical guide instrument is positioned on the transverse cut surface of the tibia. In some embodiments, the method may further comprise displaying, by the surgical navigation system, the position of the surgical guide instrument relative to the patient's bone. In some embodiments, the method may further comprise displaying, by the surgical navigation system, an indication of a predetermined position for the surgical guide instrument relative to the position of the surgical guide instrument. In some embodiments, the method may further comprise indicating, by the surgical navigation system, when the surgical guide instrument is positioned at the predetermined position for the surgical guide instrument.

According to yet another aspect, a surgical instrument for an orthopaedic surgical procedure may comprise an elongated body extending from a first end to a second end. The elongated body may comprise an inner wall extending inwardly from an opening defined in the first end of the elongated body, where the inner wall defines a bore sized to receive a shaft of a second surgical instrument such that the navigated pointer instrument is held in a predetermined position relative to the surgical instrument. The surgical instrument may further comprise a flange extending from the first end to the second end and a lug extending outward from the flange transverse to the bore.

In some embodiments, the lug may comprise an outer surface extending outward from the flange. In some embodiments, the outer surface may be cylindrical. In some embodiments, the outer surface may be tapered. In some embodiments, the outer surface of the lug may be sized to be received in a hole defined in a surgical cutting guide. In some embodiments, the surgical instrument may further comprise a second lug extending outward from the flange transverse to the bore. In some embodiments, the lug may comprise a rectangular tab extending outward from the flange. In some embodiments, the rectangular tab may be sized to be received in a keel slot defined in a surgical cutting guide. In some embodiments, the inner wall may extend to an opening defined in the second end of the elongated body, and the bore may extend through an entire length of the elongated body. In some embodiments, the first end of the elongated body may include an outer wall surrounding the opening defined in the first end, where the outer wall is configured to abut a collar on the shaft of the navigated pointer instrument when the navigated pointer instrument is placed in the predetermined position. In some embodiments, the inner wall may extend to an end wall of the elongated body, and the inner wall and the end wall may cooperate to define the bore. In some embodiments, an inner diameter of the bore may be sized to match an outer diameter of the shaft of the navigated pointer instrument. In some embodiments, the shaft may be free to rotate relative to the surgical instrument while the navigated pointer instrument is held in the predetermined position relative to the surgical instrument.

According to still another aspect, a surgical instrument for an orthopaedic surgical procedure may comprise an elongated body extending from a first end to a second end. The elongated body may comprise a first inner wall extending inwardly from a first opening defined in the first end, where the first inner wall defines a first slot sized to receive a shaft of another surgical instrument. The elongated body may further comprise a second inner wall extending inwardly from a second opening defined in the second end, where the second defines a second slot sized to receive a pointer end of a navigated pointer instrument such that the pointer end is held in a predetermined position relative to the surgical instrument.

In some embodiments, the another surgical instrument comprises a surgical reamer. In some embodiments, the first inner wall may extend to a first end wall, and the first inner wall and the first end wall may cooperate to define the first slot. In some embodiments, the second inner wall may extend to a second end wall, and the second inner wall and the second end wall may cooperate to define the second slot. In some embodiments, a passage may be defined between the first end wall and the second end wall, such that the first slot is in fluid communication with the second slot through the passage. In some embodiments, an inner diameter of the second slot may be sized to match an outer diameter of the pointer end. In some embodiments, the pointer end may be free to rotate relative to the surgical instrument while being held in the predetermined position relative to the surgical instrument.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
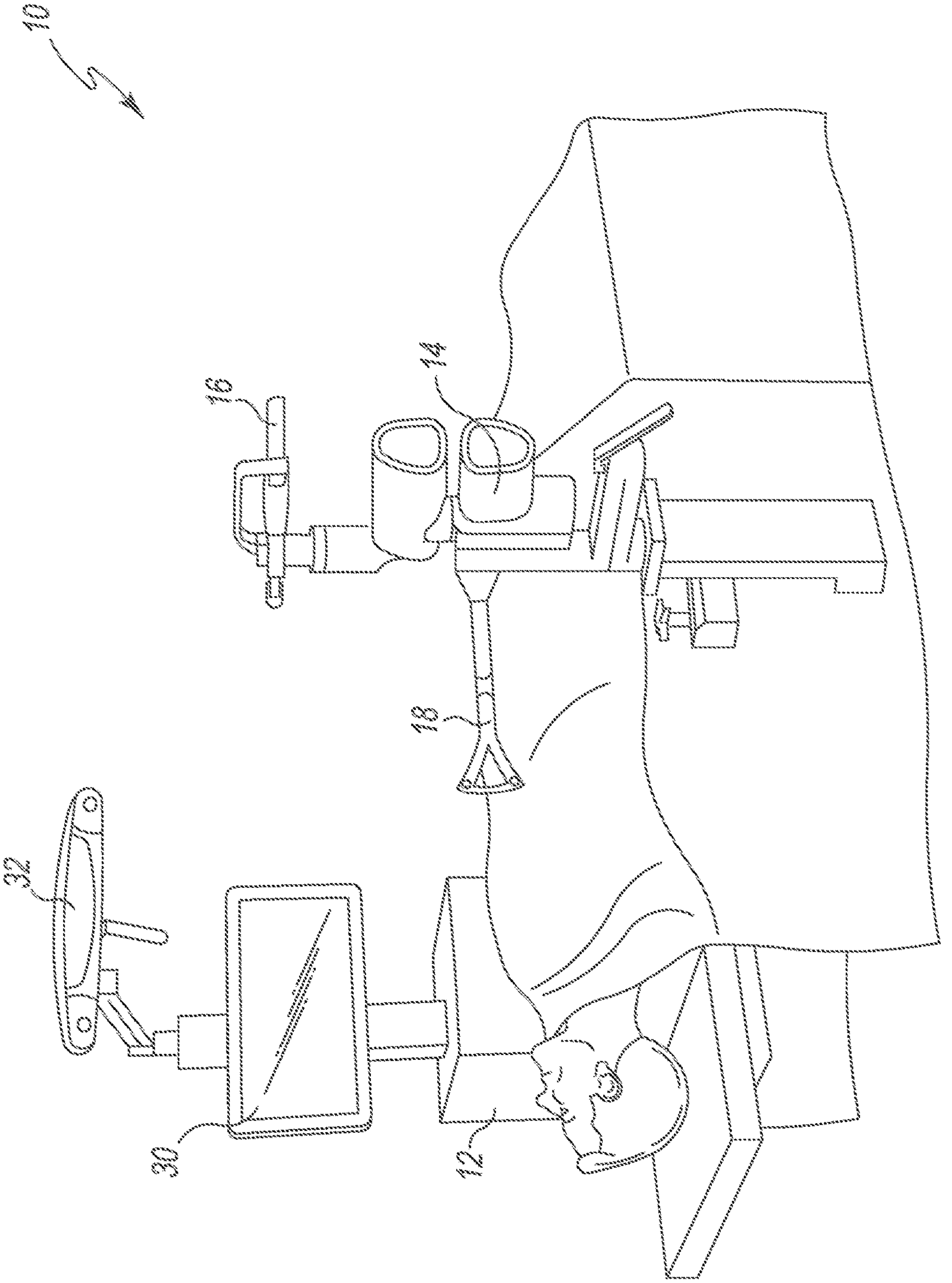
FIG. 1 is a schematic diagram of a system for planning and assisting an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical system 10 is used during an orthopaedic surgical procedure, such as a unicompartmental knee arthroplasty (UKA) procedure. During that procedure, an orthopaedic surgeon may use one or more manual instruments such as cutting blocks, finishing blocks, templates, or other instruments. As described further below, the surgeon may use the surgical system 10 for surgical navigation with manual surgical instruments, for example by tracking the location of the manual instruments and confirming that the manual instruments are used in various locations and/or orientations as indicated in a predetermined surgical plan. Accordingly, the technologies disclosed herein may provide for improved surgical navigation (e.g., improved placement accuracy and/or otherwise improved navigation) with manual surgical instruments. In some embodiments, the same manual surgical instruments may be used with both the surgical system 10 and in traditional, non-robotic-assisted surgeries. Accordingly, the technologies disclosed herein may not require custom surgical instruments specific to robotic-assisted surgery and thus may reduce costs for robotic-assisted surgery.

As shown in FIG. 1, the system 10 includes a surgical planning and assistance device 12, a robotic surgical device 14, and may include multiple registration tools 18. The surgical planning and assistance device 12 may be embodied as any type of computer system capable of performing the functions described herein. For example, the surgical planning and assistance device 12 may be embodied as, without limitation, a workstation, a desktop computer, a laptop computer, a special-purpose compute device, a server, a rack-mounted server, a blade server, a network appliance, a web appliance, a tablet computer, a smartphone, a consumer electronic device, a distributed computing system, a multiprocessor system, and/or any other computing device capable of performing the functions described herein. Accordingly, the illustrative surgical planning and assistance device 12 may include components commonly found in a computer such as a processor, an I/O subsystem, memory, a data storage device, a communication subsystem, and various input/output devices. Additionally, although the surgical planning and assistance device 12 is illustrated in FIG. 1 as embodied as a single computer, it should be appreciated that the surgical planning and assistance device 12 may be embodied as multiple devices cooperating together to facilitate the functionality described below. For example, in some embodiments, the system 10 may include a base station and a satellite station or other combination of computing devices. Additionally or alternatively, in some embodiments, the surgical planning and assistance device 12 may be embodied as a "virtual server" formed from multiple computer systems distributed across a network and operating in a public or private cloud.

As shown in FIG. 1, the surgical planning and assistance device 12 includes a display 30. The display 30 may be embodied as any type of display capable of displaying digital images or other information, such as a liquid crystal display (LCD), a light emitting diode (LED), a plasma display, a cathode ray tube (CRT), or other type of display device. In some embodiments, the display 30 may be coupled to a touch screen to allow user interaction with the surgical planning and assistance device 12.

The surgical planning and assistance device 12 further includes one or more cameras 32. Each of the cameras 32 may be embodied as a digital camera or other digital imaging device coupled to the surgical planning and assistance device 12. Each camera 32 includes an electronic image sensor, such as an active-pixel sensor (APS), e.g., a complementary metal-oxide-semiconductor (CMOS) sensor, or a charge-coupled device (CCD). In the illustrative embodiment, multiple cameras 32 are arranged in an array and are thus capable of determining distance to objects imaged by the cameras 32.

The robotic surgical device 14 may be embodied as any type of robot capable of performing the functions described herein. Illustratively, the robotic surgical device 14 is embodied as a robotic arm that may be attached to a surgical table or otherwise positioned near a patient during the orthopaedic surgical procedure. The robotic surgical device 14 includes a surgical tool 16, illustratively embodied as a surgical saw 16. In use, the robotic surgical device 14 supports the surgical saw 16 and may constrain movement of the surgical saw 16 within a resection plane specified in a surgical plan. The surgeon may activate the surgical saw 16 and perform the resection with the surgical saw 16 while the robotic surgical device 14 constrains movement of the surgical saw 16 to the resection plane. Although illustrated with a surgical saw 16, it should be understood that, in other embodiments, the robotic surgical device 14 may include, or be used with, one or more other surgical instruments, such as, for example, surgical burrs, chisels, impactors, reamers, and other powered surgical tools. The robotic surgical device 14 may illustratively be embodied as a VELYS™ Robotic-Assisted Solution, commercially available from DePuy Synthes Products, Inc. of Warsaw, Indiana.

The surgical planning and assistance device 12 and the robotic surgical device 14 may be configured to transmit and receive data with each other and/or other devices of the system 10 over a network. The network may be embodied as any number of various wired and/or wireless networks. For example, the network may be embodied as, or otherwise include, a wired or wireless local area network (LAN), a wired or wireless wide area network (WAN), a cellular network, and/or a publicly-accessible, global network such as the Internet. As such, the network include any number of additional devices, such as additional computers, routers, stations, and switches, to facilitate communications among the devices of the system 10.

The system 10 further includes a number of registration tools 18. As described further below, in use, the surgical planning and assistance device 12 may track the location of the registration tools 18 in space using the array of cameras 32. For example, each registration tool 18 may include a number of hydrophobic optical reflectors arranged in a predetermined pattern visible to the cameras 32. Illustratively, the registration tools 18 include a marker 18 secured to the robotic device 14, which may allow the device 12 to track the location of the robotic device 14 and/or the associated surgical tool 16. The system 10 may also track multiple arrays configured to each be secured to one of the patient's bones or, as described further below, a pointer that may be temporarily positioned by a surgeon relative to anatomical landmarks of the patient while the pointer is observed by the cameras 32. As such, the registration tools 18 may be used for registration and tracking of the patient's bony anatomy during the orthopaedic surgical procedure. Although illustrated as including registration tools 18 suitable for optical tracking with the cameras 32, it should be understood that in some embodiments, the system 10 may use electromagnetic tracking or other position tracking technology for tracking the registration tools 18.

Figure 2:
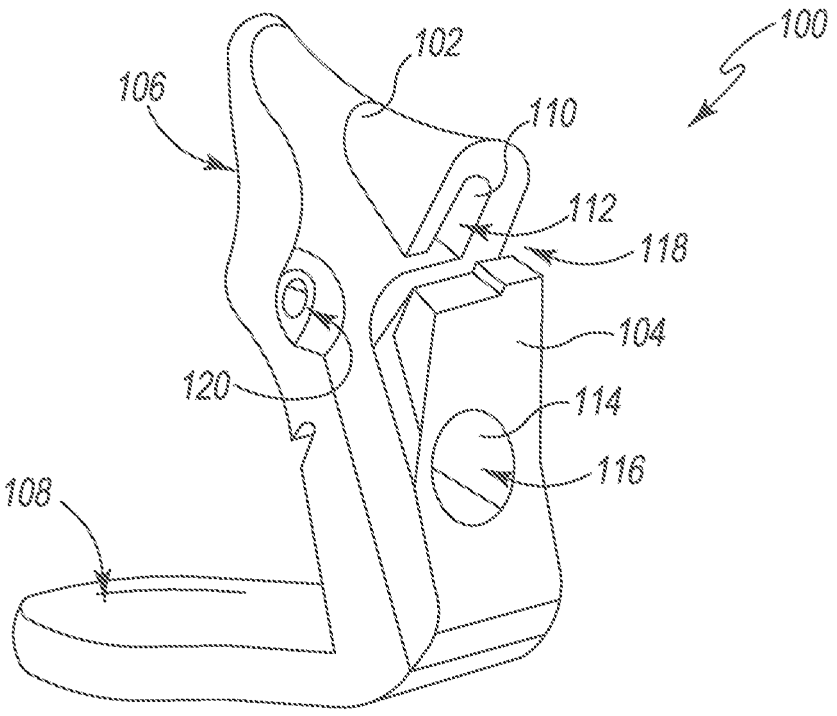
FIG. 2 is a perspective diagram of a femoral finishing block that may be used during an orthopaedic surgical procedure.

Referring now to FIG. 2, the system 10 may be used with an illustrative femoral finishing block 100. As described further below, during a unicompartmental knee arthroplasty (UKA) surgical procedure, the finishing block 100 may be attached to a surgically prepared distal end of a patient's femur. The finishing block 100 includes various cutting guides, drill guides, and/or other surgical guides that may be used to further surgically prepare the patient's femur.

The finishing block 100 includes a body 102, which is illustratively formed from a metallic material. In some embodiments, the body 102 may be formed from a polymeric material or other dimensionally stable material that is suitable for use as a surgical guide. The body 102 includes an outer surface 104 and multiple bone-contacting surfaces 106, 108. More particularly, the distal-contacting surface 106 is configured to contact the surgically prepared distal cut surface of the patient's femur, and the posterior-contacting surface 108 is configured to contact a surgically prepared posterior cut surface of the patient's femur.

As described above, the finishing block 100 includes various surgical guides defined in the body 102. An inner wall 110 extends through the body 102 from the outer surface 104 to the distal-contacting surface 106. The inner wall 110 defines an anterior peg hole 112. Similarly, an inner wall 114 extends from the outer surface 104 to the distal-contacting surface 106 and defines a posterior peg hole 116. The peg holes 112, 116 are surgical guides that may be used by a surgeon to drill, ream, or otherwise prepare peg holes in the distal end of the patient's femur to receive pegs of a prosthetic component.

The body 102 further includes a posterior chamfer cutting slot 118 defined through the body 102, from the outer surface 104 to the distal-contacting surface 106. This cutting slot 118 is an open-ended slot that may be used by the surgeon as a captive cutting guide to perform the posterior chamfer cut to the patient's femur. (In some embodiments, however, the posterior chamfer cut may be performed using the robotic surgical device 14, rather than the finishing block 100.) The finishing block 100 may include one or more additional cutting guides, including captured cutting guides (e.g., slots, holes, etc.), and non-captured cutting guides (e.g., surfaces, edges, etc.). For example, the body 102 may include a posterior cutting slot and an anterior cutting slot along with the posterior chamfer cutting slot 118.

The finishing block 100 further includes one or more mounting pin holes 120 defined through the body 102 from the outer surface 104 to the distal-contacting surface 106 and/or the posterior-contacting surface 108. Each of those mounting pin holes 120 may be configured to receive a surgical pin, a bone screw, or other fastener for fixing the finishing block 100 in position against the surgically prepared distal end of the femur.

Figure 3:
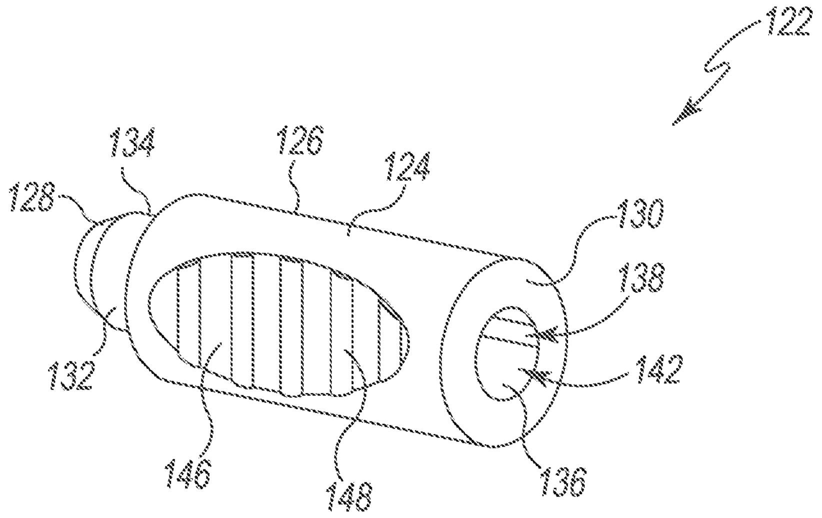
FIG. 3 is a perspective diagram of a surgical instrument adapter that may be used during an orthopaedic surgical procedure.

Referring now to FIG. 3, a surgical instrument adapter 122 includes an elongated body 124, which may be formed from a polymeric material such as polyphenylsulfone (PPSU). The adapter 122 may be molded, additively manufactured, or otherwise manufactured. In some embodiments, the adapter 122 may be formed from a metallic material.

The body 124 includes a roughly cylindrical outer surface 126 that extends from an end 128 to another end 130. A lug 132 is positioned at the end 128, extending outward from the body 124. The lug 132 includes an outer surface 134, which may be cylindrical or tapered. In some embodiments, the lug 132 may be formed to include a groove (e.g., intersecting a longitudinal axis of the lug 132) such that portions of the lug 132 can deform toward one another when the lug 132 is inserted into a hole of another surgical instrument. In such embodiments, a diameter of the lug 132 may be slightly larger than a diameter of the hole to enable a press-fit contact between the adapter 122 and the other surgical instrument.

Figure 5:
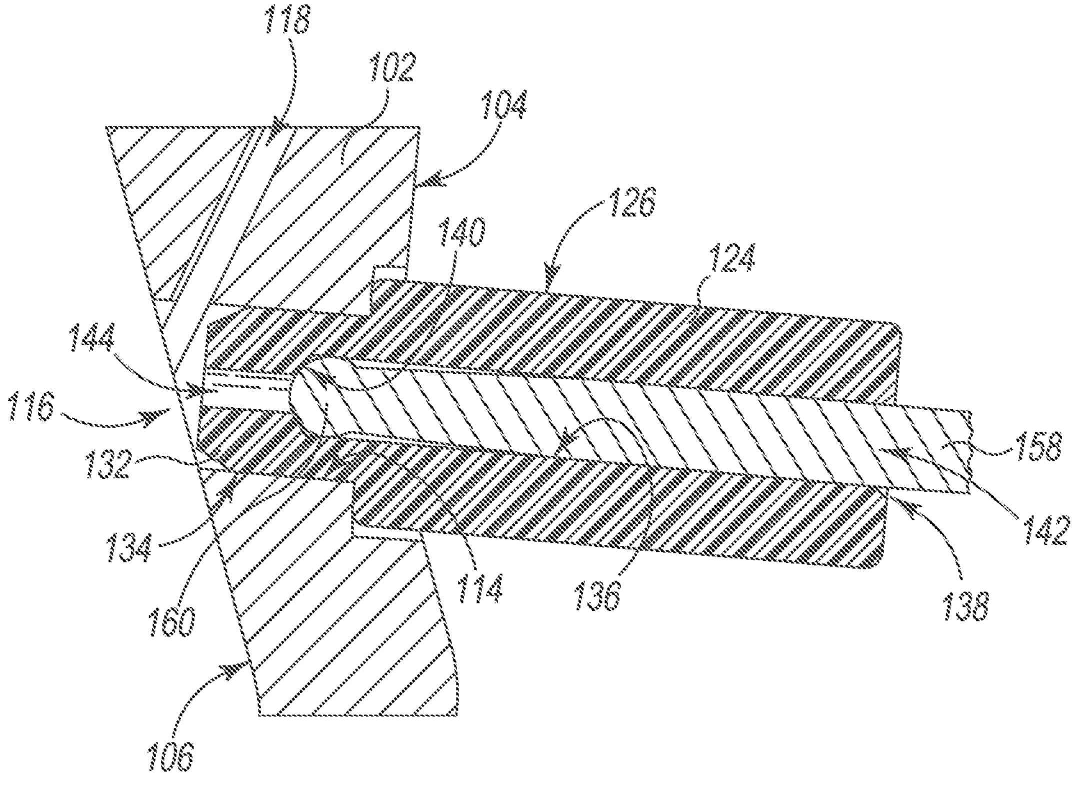
FIG. 5 is a cross-sectional diagram of the surgical instrument assembly of FIG. 4.

An inner wall 136 extends inwardly into the body 124 from an opening 138 defined in the end 130 until reaching an end wall 140, which is shown in FIG. 5. The inner wall 136 and the end wall 140 cooperate to define a slot 142 that extends linearly from the end 130 toward the end 128 and the lug 132. As shown in FIG. 5, a port 144 is defined in the end wall 140. The port 144 allows communication (e.g., air or fluid) between the slot 142 and the exterior of the body 124. In embodiments where the adapter 122 is reusable, the port 144 may assist with reprocessing of the adapter 122 (e.g., improving ease of cleaning the adapter 122).

The outer surface 126 further includes a scalloped cutout surface 146. Multiple ridges 148 are defined on cutout surface 146. Those features 146, 148 may provide improved grip to a surgeon or other users. Additionally or alternative, in other embodiments, the adapter 122 may include knurling, texture, or other features to improve grip.

Figure 4:
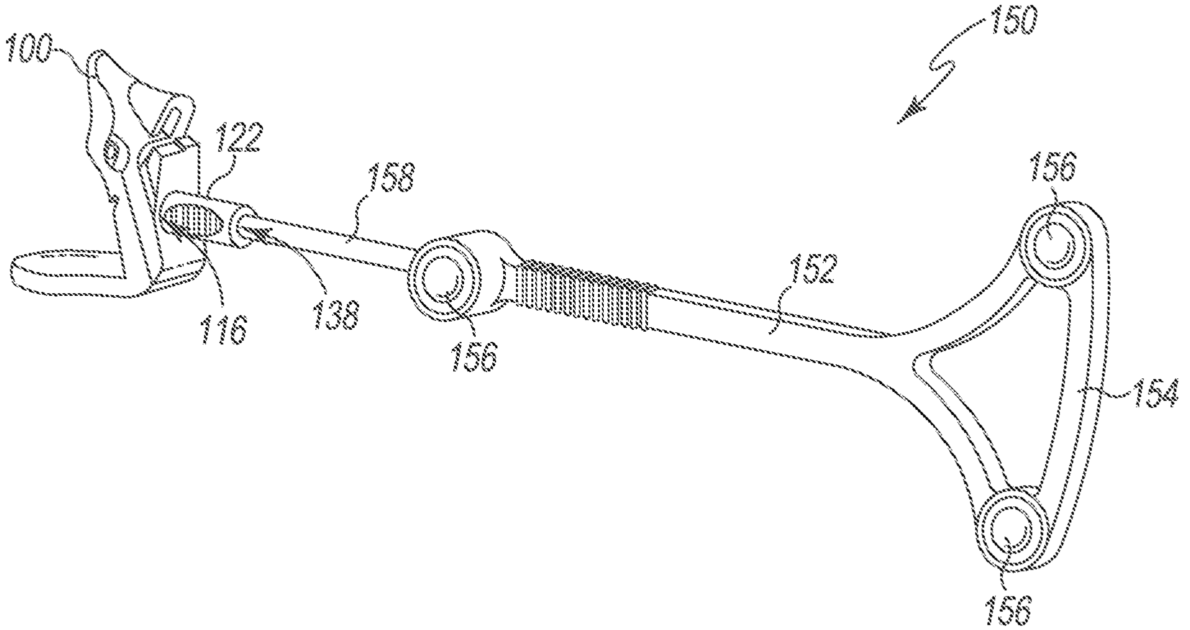
FIG. 4 is a perspective diagram of a surgical instrument assembly including the femoral finishing block of FIG. 2, the surgical instrument adapter of FIG. 3, and a pointer registration tool.

Referring now to FIGS. 4-8, in use, the surgical instrument adapter 122 may be used with the finishing block 100 and the system 10 to perform a UKA orthopeadic surgical procedure. As part of the UKA procedure, a surgeon or other user assembles the surgical instrument adapter 122 with the finishing block 100 and a pointer 150, as shown in FIGS. 4 and 5.

The pointer 150 is a registration tool 18 that may be used with the system 10 for surgical navigation and/or robotic assisted surgery. The illustrative pointer 150 includes an elongated body 152 that is coupled to a triangular frame 154. The frame 154 supports hydrophobic optical reflectors 156, which may be tracked by the device 12 using the cameras 32 as described above. The pointer 150 further includes an elongated shaft 158 that extends to a tip 160. In use, the surgeon positions the tip 160 of the pointer 150 in a desired location. The device 12, using the camera 32, tracks the location of the reflectors 156 and, based on those tracked locations, determines the corresponding position of the tip 160.

To assemble the adapter 122 and the pointer 150, the tip 160 of the pointer 150 is inserted through the opening 138 into the slot 142 of the adapter 122. The pointer 150 is inserted until the tip 160 contacts the end wall 140, which retains the tip 160 of the pointer 150 at a predetermined position relative to the adapter 122 (within manufacturing tolerances). In some embodiments, the pointer 150 may be free to rotate relative to the adapter 122 while the tip 160 is held in the predetermined position relative to the adapter 122. As the tip 160 is inserted into the slot 142, air may escape through the port 144, which may improve ease of insertion of the pointer 150. To assemble the adapter 122 with the finishing block 100, the lug 132 of the adapter 122 is inserted into the peg hole 116 of the finishing block 100. When inserted, the outer wall 134 of the lug 132 engages with the inner wall 114 of the peg hole 116. In some embodiments, the outer wall 134 may be tapered and thus may be friction locked into the peg hole 116. In some embodiments, the outer wall 134 may be tapered to promote friction-lock in the peg hole 116. As described above, in some embodiments, the lug 132 may additionally or alternatively include a groove that allows portions of the lug 132 to deform toward one another when the lug 132 is inserted into the peg hole 116. The diameter of the lug 132 may be slightly larger than the diameter of the peg hole 166 to enable a press-fit contact between the adapter 122 and the finishing block 100.

Figure 6:
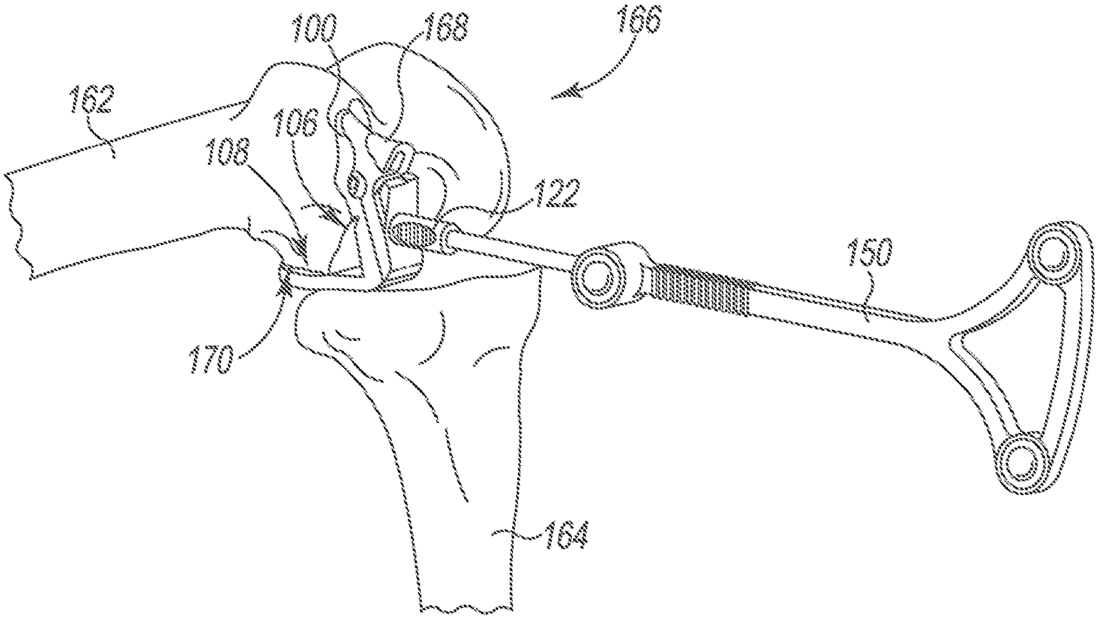
FIG. 6 is a perspective diagram of the surgical instrument assembly of FIGS. 4-5 in use during an orthopaedic surgical procedure.

During the UKA surgical procedure, the surgeon exposes part or all of a patient's knee joint, including a femur 162 and a tibia 164 as shown in FIG. 6. The surgeon surgically prepares a distal end 166 of the femur 162 by performing a distal resection, which exposes a surgically prepared distal surface 168, and a posterior resection, which exposes a surgically prepared posterior surface 170. As shown in FIG. 6, the surgeon places the finishing block 100, assembled with the adapter 122 and the pointer 150, onto the distal cut surface 168 and the posterior cut surface 170. When in position, the distal-contacting surface 106 of the finishing block 100 contacts the distal cut surface 168, and the posterior-contacting surface 108 of the finishing block 100 contacts the posterior cut surface 170 of the femur 162.

Figure 7:
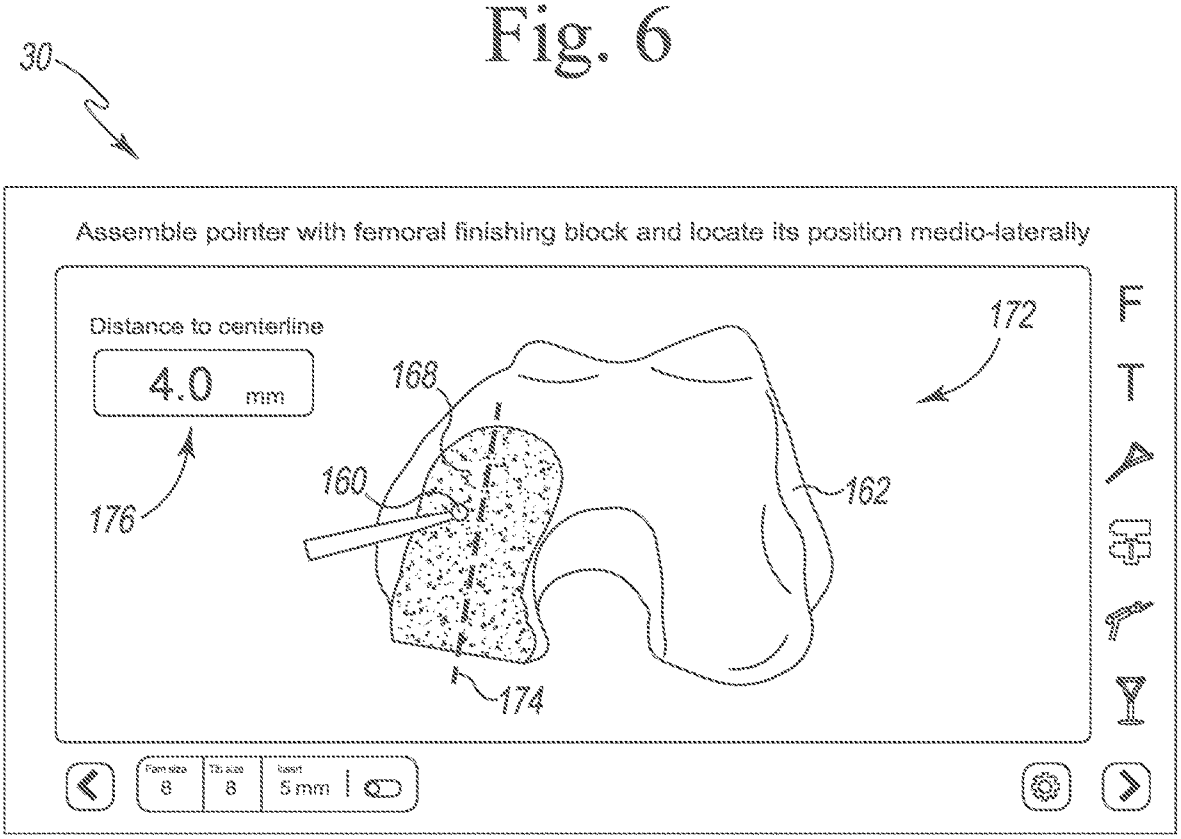
FIGS. 7 and 8 are illustrative graphical user interfaces that may be provided by the system of FIG. 1 for use during the orthopaedic surgical procedure shown in FIG. 6.
Figure 8:
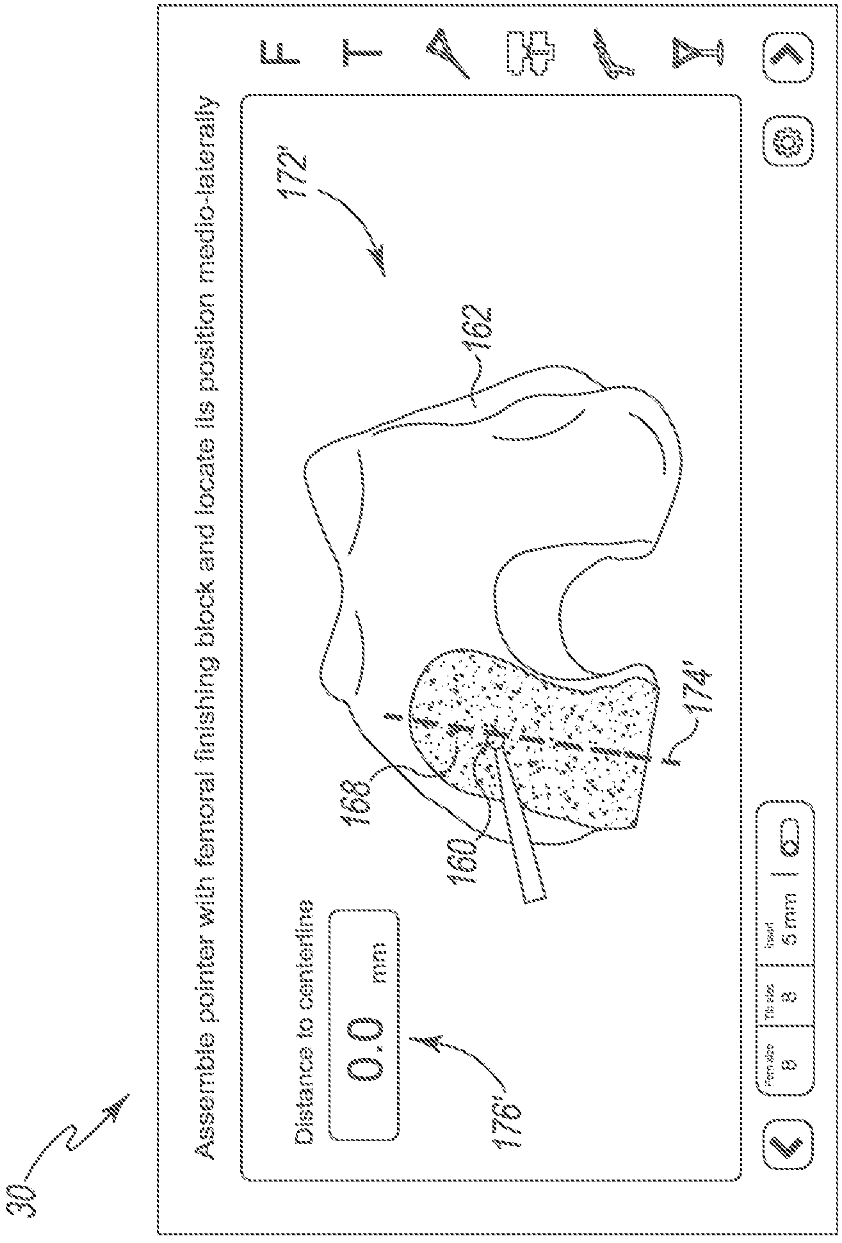

As shown in FIGS. 7 and 8, the surgeon uses the system 10 to determine the appropriate medial/lateral position for the finishing block 100. As shown, the display 32 of the device 12 displays a user interface 172. The user interface 172 includes a graphical representation of the femur 162 along with the surgically prepared distal surface 168. The user interface 172 further displays a planned centerline 174 relative to the femur 162. The planned centerline 174 may be based on a predetermined surgical plan, preoperative data, or otherwise determined by the surgeon, and represents the desired final position of a centerline of the finishing block 100.

The user interface 172 further includes a representation of the tip 160 of the pointer 150. The representation of the tip 160 is rendered by the device 12 relative to the representation of the femur 162 based on the actual position of the pointer 150 determined using the tracking cameras 132. The user interface 172 is updated as the surgeon moves the pointer 150 (and thus the attached adapter 122 and finishing block 100) relative to the surgically prepared distal surface 168. As shown, the user interface 172 further includes a distance display 176, which illustratively displays the distance between the current position of the tip 160 of the pointer 150 and the planned centerline 174 in millimeters. The user interface 172 may include any other additional information displays, graphical representations, or other information to assist the surgeon in placing the finishing block 100.

As shown in FIG. 8, when the surgeon positions the tip 160 of the pointer 150 in position on the planned centerline, the user interface 172' may be updated in order to indicate successful positioning. Illustratively, the planned centerline 174' is rendered in a different color and the distance display 176' indicates zero distance; however, in other embodiments any other technique may be used to indicate that the finishing block 100 has been positioned in the planned position. After positioning the finishing block 100 in the desired position, the surgeon fixes the finishing block 100 in place, for example using surgical pins through one or more of the pin holes 120. The surgeon removes the adapter 122 from the finishing block 100, and then uses the finishing block 100 to continue the surgical procedure. Illustratively, the surgeon may use the finishing block 100 to perform the anterior resection and/or the posterior chamfer cut and/or to drill the anterior and posterior peg holes.

Figure 9:
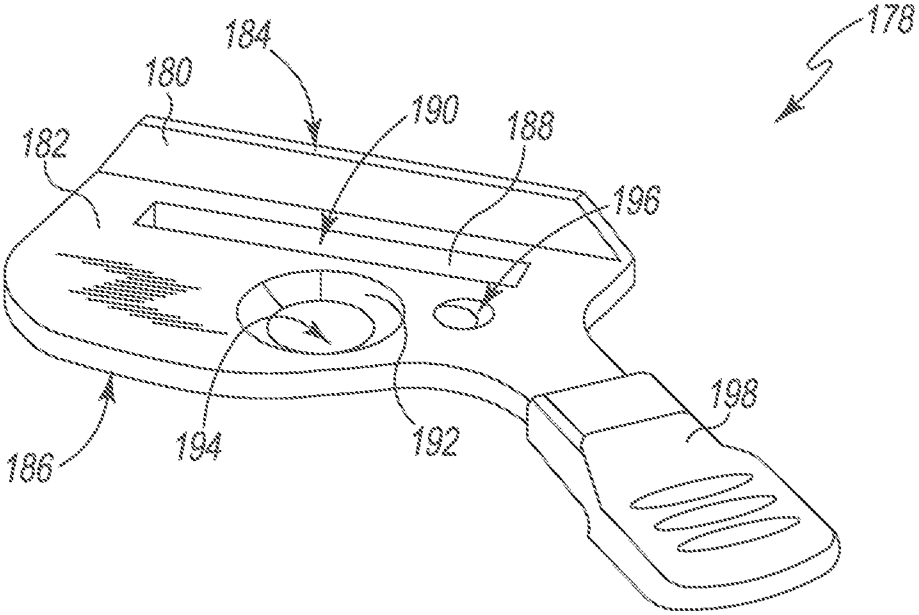
FIG. 9 is a perspective diagram of a tibial template that may be used during an orthopaedic surgical procedure.

Referring now to FIG. 9, the system 10 may also be used with an illustrative tibial template 178. As described further below, during the UKA surgical procedure, the tibial template 178 may be attached to a surgically prepared proximal end of a patient's tibia. The tibial template 178 includes various cutting guides, drill guides, and/or other surgical guides that may be used to further surgically prepare the patient's tibia.

The tibial template 178 includes a body 180, which is illustratively formed from a metallic material. In some embodiments, the body 180 may be formed from a polymeric material or other dimensionally stable material that is suitable for use as a surgical guide. The body 180 includes an outer surface 182 that is opposite a bone-contacting surface 184. The body 180 also includes a bone-contacting surface 186. Each of the bone-contacting surfaces 184, 186 is configured to contact a corresponding surgically prepared surface at a proximal end of the patient's tibia.

The tibial template 178 includes various surgical guides defined in the body 180. An inner wall 188 extends through the body 180 from the outer surface 182 to the transverse cut bone-contacting surface 186, and defines a rectangular keel slot 190. Similarly, an inner wall 192 extends through the body 180 from the outer surface 182 to the bone-contacting surface 186 and defines a tibial peg hole 194. The keel slot 190 and the peg hole 194 are surgical guides that may be used by a surgeon to cut, broach, drill, ream, or otherwise surgically prepare the proximal end of the patient's tibia to receive a prosthetic component.

The tibial template 178 further includes one or more mounting pin holes 196 defined through the body 180 from the outer surface 182 to the bone-contacting surface 186. Each of those mounting pin holes 196 may be configured to receive a surgical pin, a bone screw, or other fastener for fixing the tibial template 178 in position against the surgically prepared proximal end of the tibia. As shown, the tibial template 178 further includes a handle 198, which may be used by the surgeon to position the tibial template 178.

Figure 10:
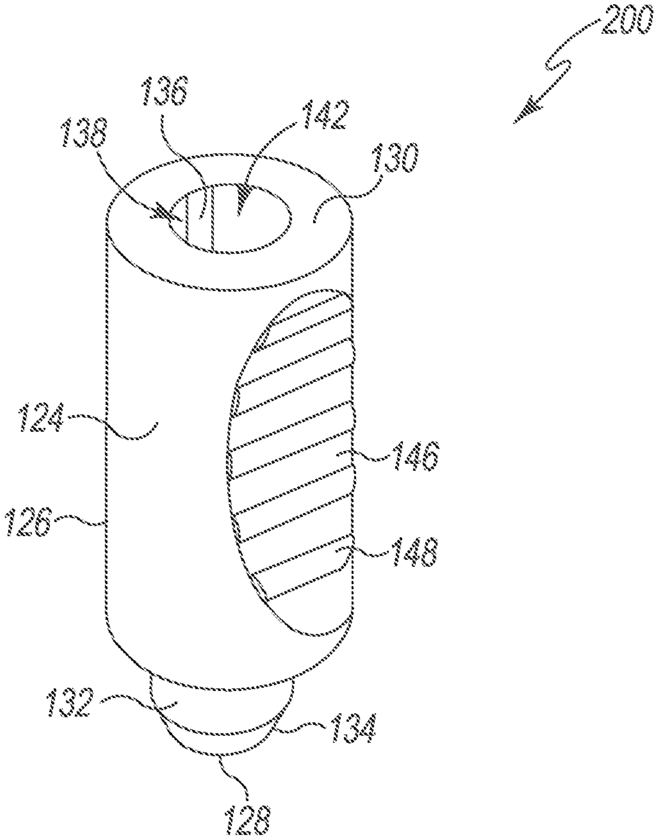
FIG. 10 is a perspective diagram of another surgical instrument adapter that may be used during an orthopaedic surgical procedure.

Referring now to FIG. 10, a surgical instrument adapter 200 includes the same or similar features as the surgical instrument adapter 122 of FIGS. 3-6, the description of which is also applicable to the surgical instrument adapter 200. Accordingly, so as not to obscure the present disclosure, description of those features is not repeated herein. In some embodiments, the surgical instrument adapter 200 may be the same device as the surgical instrument adapter 122 (e.g., the same physical device, multiple instances of the same model of device, or similar). Additionally or alternatively, the surgical instrument adapter 200 may include similar features but with different dimensions. For example, in an embodiment the surgical instrument adapter 200 may include a lug 132 that is sized for use with the tibial template 178 as described further below.

Figure 11:
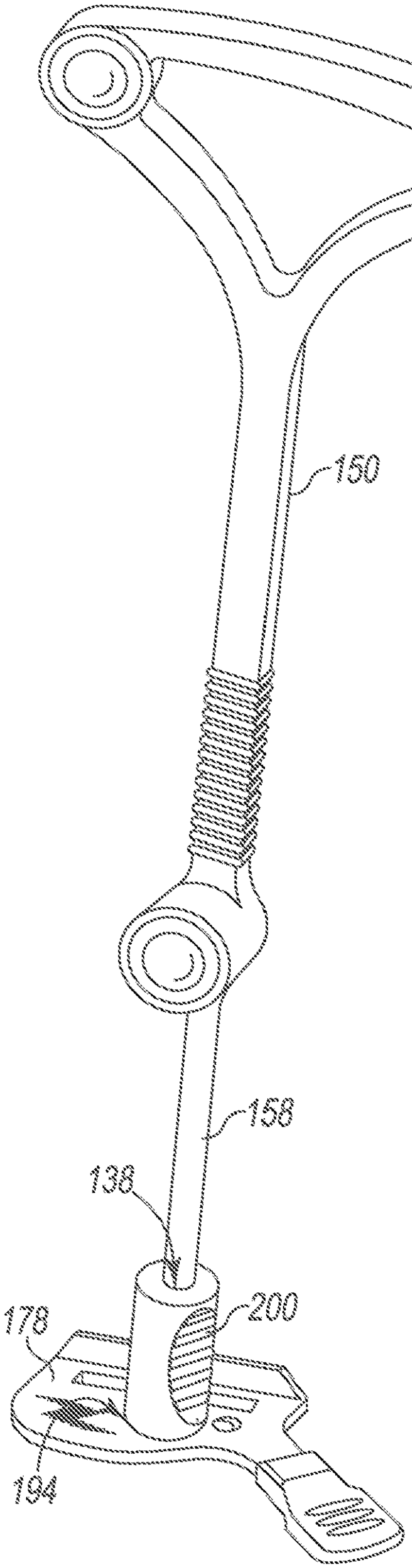
FIG. 11 is a perspective diagram of a surgical instrument assembly including the tibial template of FIG. 9, the surgical instrument adapter of FIG. 10, and the pointer registration tool.
Figure 12:
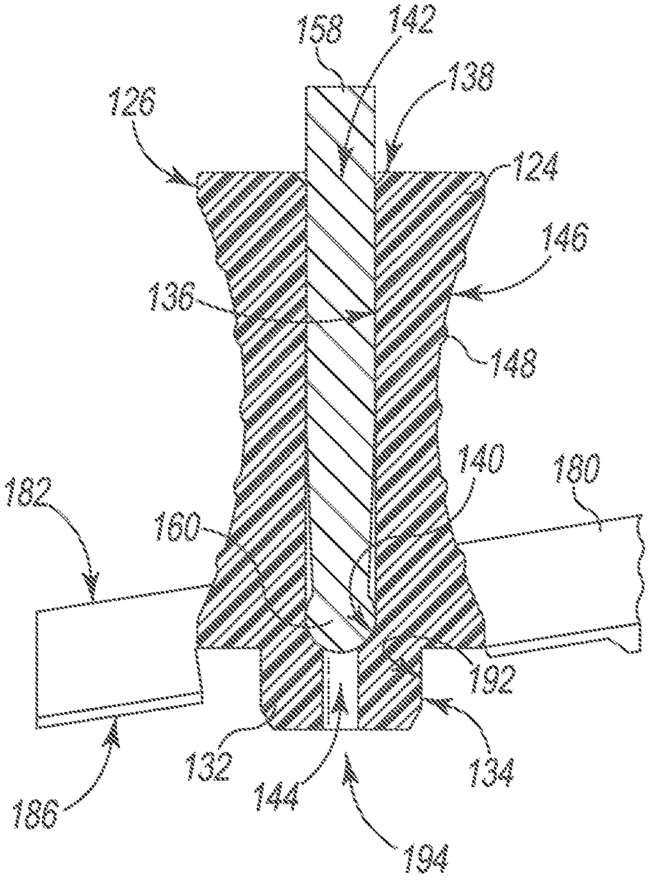
FIG. 12 is a cross-sectional diagram of the surgical instrument assembly of FIG. 11.

Referring now to FIGS. 11-15, in use, the surgical instrument adapter 200 may be used with the tibial template 178 and the system 10 to perform the UKA orthopeadic surgical procedure. As part of the UKA procedure, a surgeon or other user assembles the surgical instrument adapter 200 with the tibial template 178 and a pointer 150, as shown in FIGS. 11 and 12. The pointer 150 may be the same pointer 150 used in connection with the femoral finishing block 100 or another pointer 150 with similar features.

To assemble the adapter 200 and the pointer 150, the tip 160 of the pointer 150 is inserted through the opening 138 into the slot 142 of the adapter 200. The pointer 150 is inserted until the tip 160 contacts the end wall 140, which retains the tip 160 of the pointer 150 at a predetermined position relative to the adapter 200 (within manufacturing tolerances). In some embodiments, the pointer 150 may be free to rotate relative to the adapter 200 while the tip 160 is held in the predetermined position relative to the adapter 200. As the tip 160 is inserted into the slot 142, air may escape through the port 144, which may improve ease of insertion of the pointer 150. To assemble the adapter 200 with the tibial template 178, the lug 132 of the adapter 200 is inserted into the peg hole 194 of the tibial template 178. When inserted, the outer wall 134 of the lug 132 engages with the inner wall 192 of the peg hole 194. In some embodiments, the outer wall 134 may be tapered to promote friction-lock in the peg hole 194. As described above, in some embodiments, the lug 132 may additionally or alternatively include a groove that allows portions of the lug 132 to deform toward one another when the lug 132 is inserted into the peg hole 194. The diameter of the lug 132 may be slightly larger than the diameter of the peg hole 194 to enable a press-fit contact between the adapter 200 and the tibial template 178.

Figure 13:
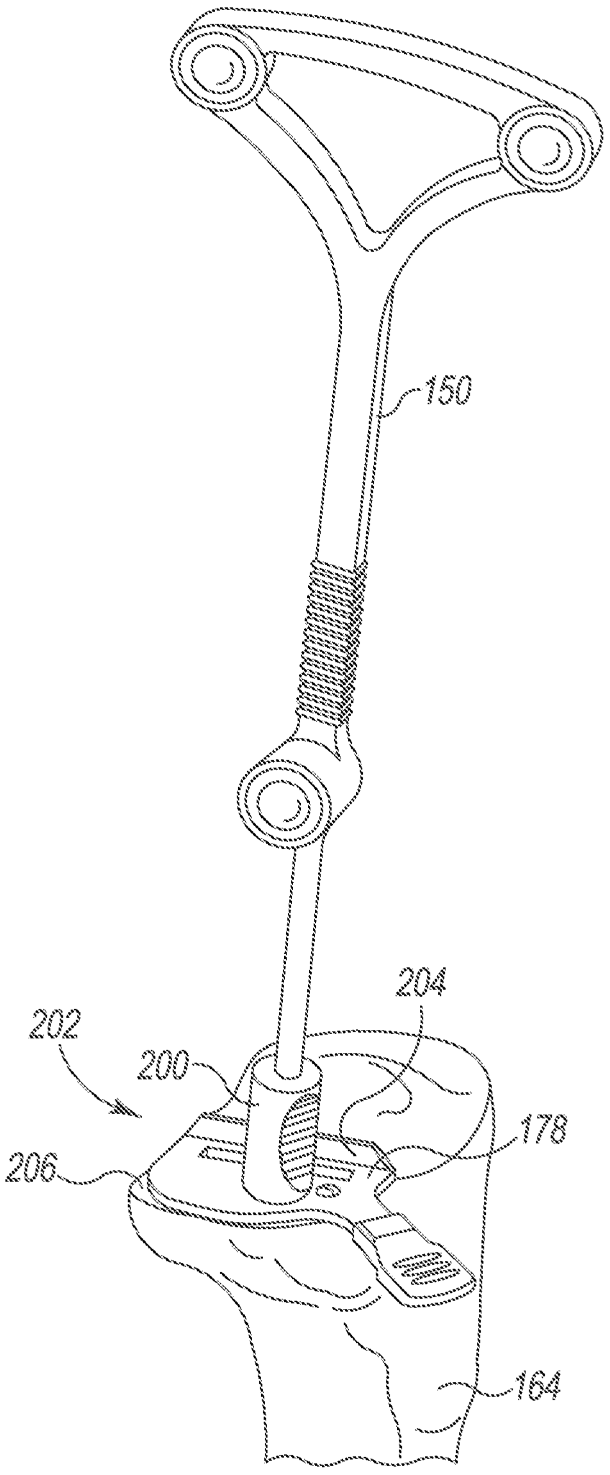
FIG. 13 is a perspective diagram of the surgical instrument assembly of FIGS. 11-12 in use during an orthopaedic surgical procedure.

During the UKA surgical procedure, the surgeon exposes part or all of a patient's knee joint, including the tibia 164 as shown in FIG. 13. The surgeon surgically prepares a proximal end 202 of the tibia 164 by performing a sagittal or vertical cut, which exposes a surgically prepared sagittal surface 204, and a transverse cut, which exposes a surgically prepared transverse surface 206. As shown in FIG. 13, the surgeon places the tibial template 178, assembled with the adapter 200 and the pointer 150, onto the transverse cut surgically prepared surface 206. When in position, the bone-contacting surface 186 of the tibial template 178 contacts the transverse cut surface 206, and the bone-contacting surface 184 of the tibial template 178 contacts the sagittal cut surface 204.

Figure 14:
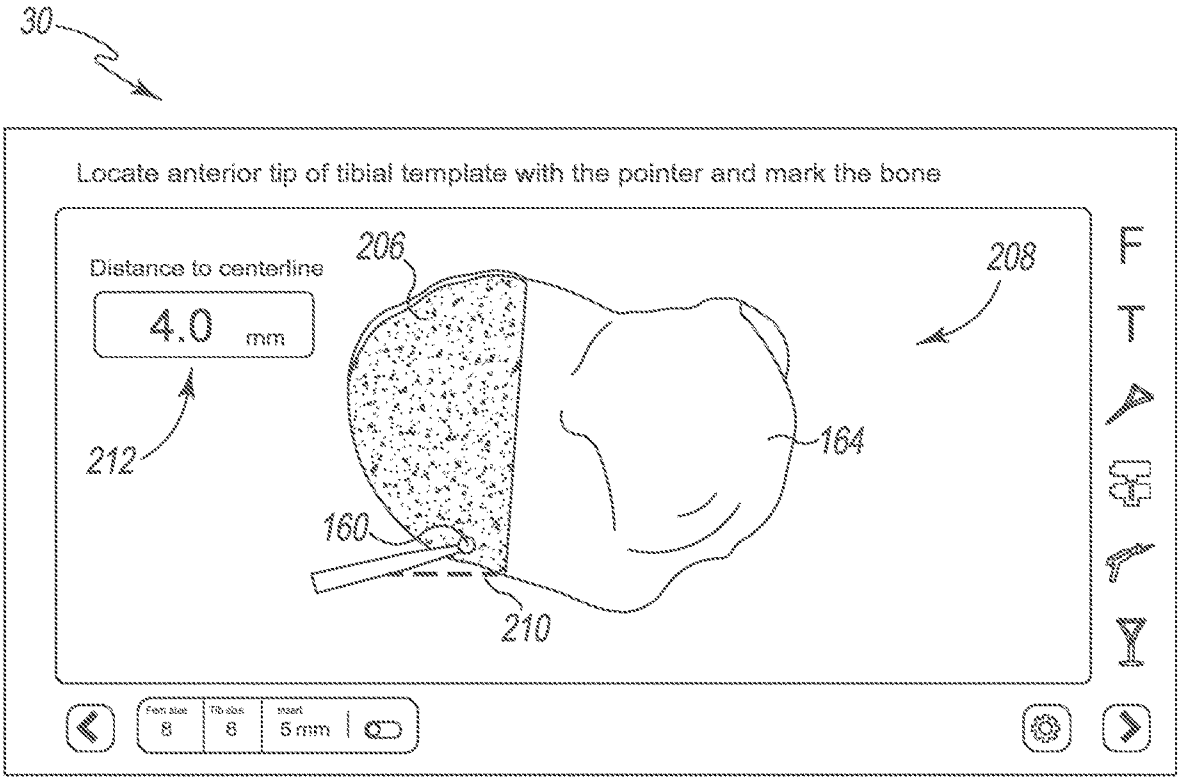
FIGS. 14 and 15 are illustrative graphical user interfaces that may be provided by the system of FIG. 1 for use during the orthopaedic surgical procedure shown in FIG. 13.
Figure 15:
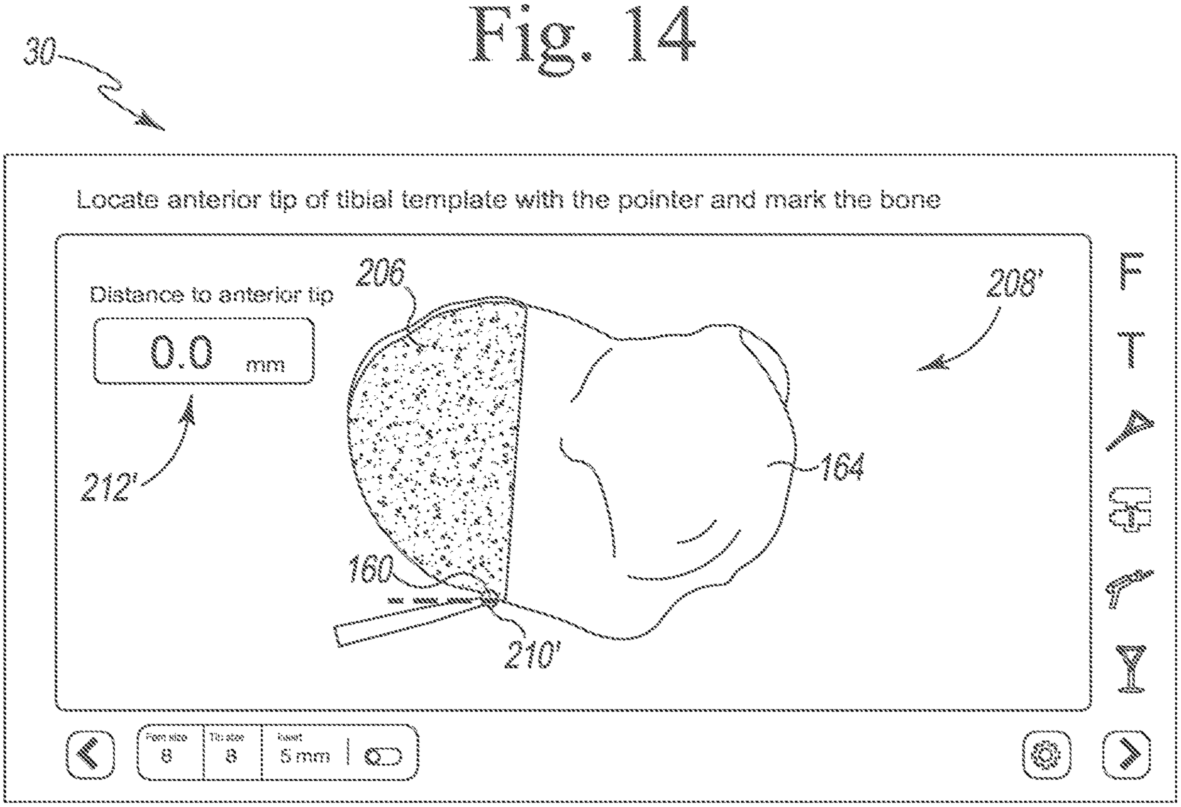

As shown in FIGS. 14 and 15, the surgeon uses the system 10 to determine the appropriate anterior/posterior position for the tibial template 178. As shown, the display 32 of the device 12 displays a user interface 208. The user interface 208 includes a graphical representation of the tibia 164 along with the surgically prepared surface 206. The user interface 208 further displays a planned anterior tip line 210 relative to the tibia 164. The planned anterior tip line 210 may be based on a predetermined surgical plan, preoperative data, or otherwise determined by the surgeon, and represents the desired final position of an anterior tip of the tibial template 178.

The user interface 208 further includes a representation of the tip 160 of the pointer 150. The representation of the tip 160 is rendered by the device 12 relative to the representation of the tibia 164 based on the actual position of the pointer 150 determined using the tracking cameras 132. The user interface 208 is updated as the surgeon moves the pointer 150 (and thus the attached adapter 200 and tibial template 178) relative to the surgically prepared surface 206. As shown, the user interface 208 further includes a distance display 212, which illustratively displays the distance between the current position of the tip 160 of the pointer 150 and the planned anterior tip line 210 in millimeters. The user interface 208 may include any other additional information displays, graphical representations, or other information to assist the surgeon in placing the tibial template 178.

As shown in FIG. 15, when the surgeon positions the tip 160 of the pointer 150 in position on the planned anterior tip line, the user interface 208' may be updated in order to indicate successful positioning. Illustratively, the planned anterior tip line 210' is rendered in a different color and the distance display 212' indicates zero distance; however, in other embodiments any other technique may be used to indicate that the tibial template 178 has been positioned in the planned position. After positioning the tibial template 178 in the desired position, the surgeon fixes the tibial template 178 in place, for example using surgical pins through one or more pin holes. The surgeon removes the adapter 200 from the tibial template 178, and then uses the tibial template 178 to continue the surgical procedure. Illustratively, the surgeon uses the tibial template 178 to cut the keel slot and to drill the tibial peg hole.

Figure 16:
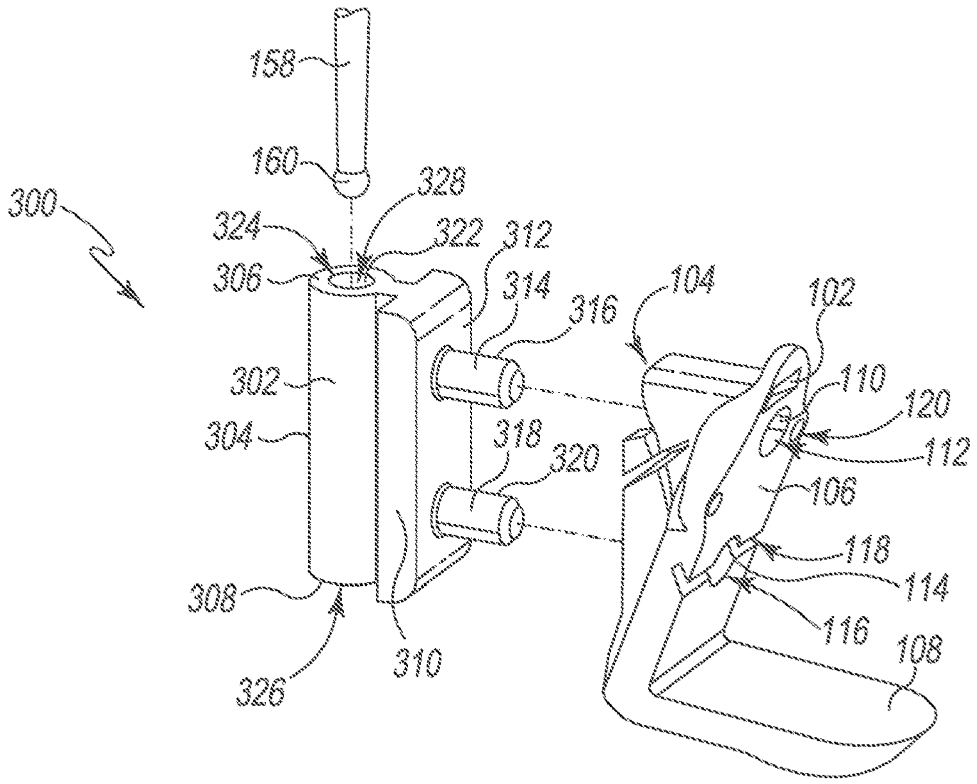
FIGS. 16 and 17 are diagrams of a surgical instrument assembly including another surgical instrument adapter, the femoral finishing block of FIG. 2, and the pointer registration tool.
Figure 17:
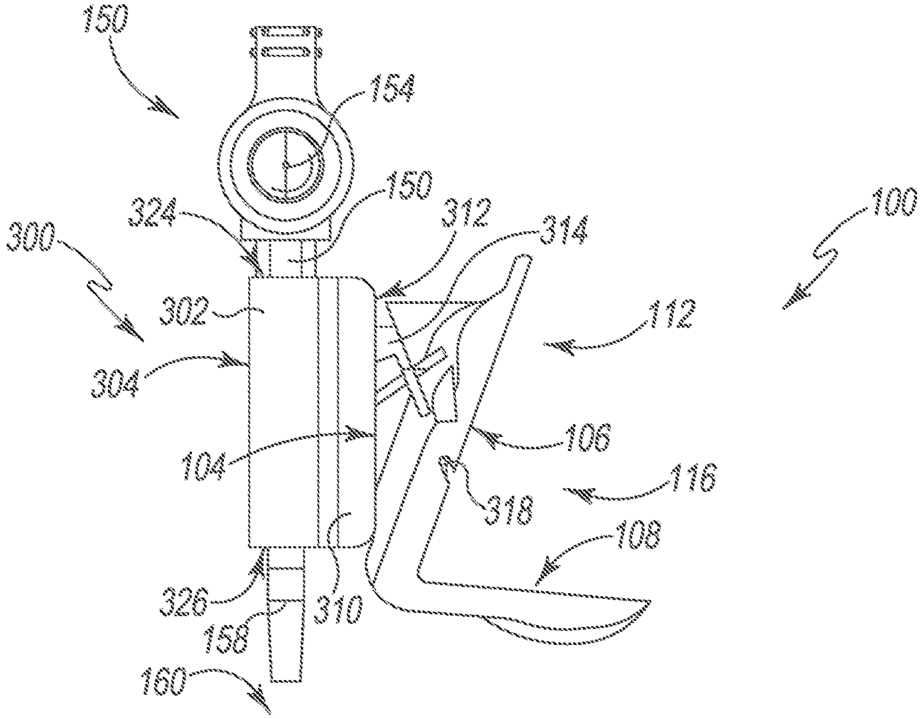

Referring now to FIGS. 16 and 17, in some embodiments, a surgical instrument adapter 300 may be assembled with the finishing block 100 and the pointer 150 in order to perform a UKA procedure. The adapter 300 includes an elongated body 302, which may be formed from a polymeric material such as polyphenylsulfone (PPSU). The adapter 300 may be molded, additively manufactured, or otherwise manufactured. In some embodiments, the adapter 300 may be formed from a metallic material.

The body 302 includes an outer surface 304 that extends from an end 306 to another end 308. A flange 310 is positioned along the body 302 between the ends 306, 308. The flange 310 includes a substantially flange surface 312. An anterior lug 314 extends outward from the flange surface 312. The anterior lug 314 includes an outer surface 316, which may be cylindrical or, in some embodiments, tapered.

Similarly, a posterior lug 318 also extends outward from the flange surface 312. The posterior lug 318 includes an outer surface 320, which may be cylindrical or, in some embodiments, tapered.

The body 302 further includes an inner wall 322 that extends from an opening 324 defined in the end 306 to another opening 326 defined in the end 308. The inner wall 322 defines a bore or through-hole 328 that extends through the body 302 from the end 306 to the end 308.

In use, as part of the UKA procedure, the surgeon or other user assembles the surgical instrument adapter 300 with the finishing block 100 and the pointer 150. To assemble the adapter 300 and the pointer 150, the tip 160 of the pointer 150 is inserted through the opening 324 into the through-hole 328 of the adapter 300. The pointer 150 is inserted until the tip 160 extends out of the through-hole 328 through the opening 326 and the shaft 158 is retained within the body 302. In some embodiments, the shaft 158 may be inserted until the end 306 of the adapter 300 contacts a flat or other feature defined on the elongated body 152 of the pointer 150. Additionally or alternatively, the shaft 158 may be inserted until the shaft 158 engages with the inner wall 322. Once inserted, the pointer 150 is retained at a predetermined position relative to the adapter 300 (within manufacturing tolerances). In some embodiments, the pointer 150 may be free to rotate relative to the adapter 122 while held in the predetermined position. To assemble the adapter 300 with the finishing block 100, the lugs 314, 318 of the adapter 300 are inserted into the peg holes 112, 116 of the finishing block 100, respectively. When inserted, the outer wall 316, 320 of each lug 314, 318 engages with the inner wall 110, 114 of the respective peg hole 112, 116. In some embodiments, the outer walls 316, 320 may each be tapered and thus may be friction locked into the respective peg holes 112, 116.

After assembling the adapter 300 with the finishing block 100 and the pointer 150, the finishing block 100 may be placed onto the surgically prepared distal surface 168 of the patient's femur 162 as described above. Also as described above, the surgeon may use the system 10 to determine the appropriate medial/lateral position for the finishing block 100. The surgeon may refer to a user interface 172 similar to that shown in FIGS. 7 and 8 in order to position the finishing block 100 according to a predetermined surgical plan.

Figure 18:
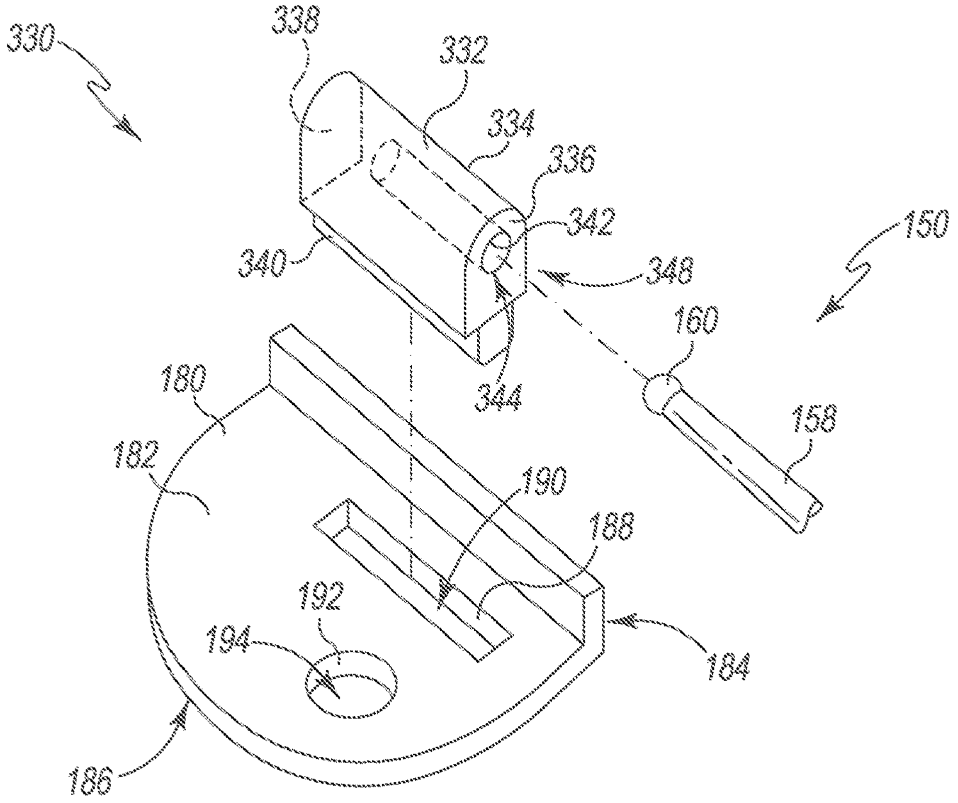
FIGS. 18, 19, and 20 are diagrams of a surgical instrument assembly including another surgical instrument adapter, the tibial template of FIG. 9, and the pointer registration tool.
Figure 19:
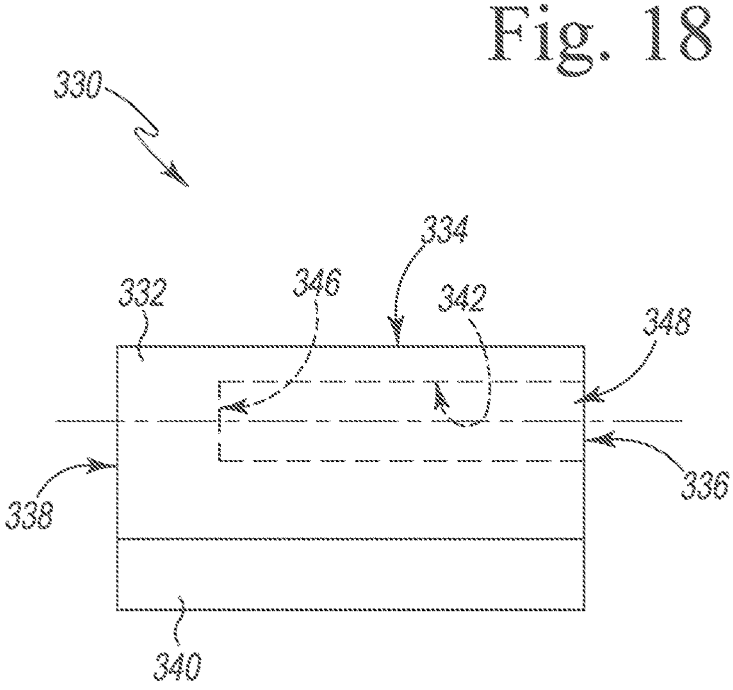
Figure 20:
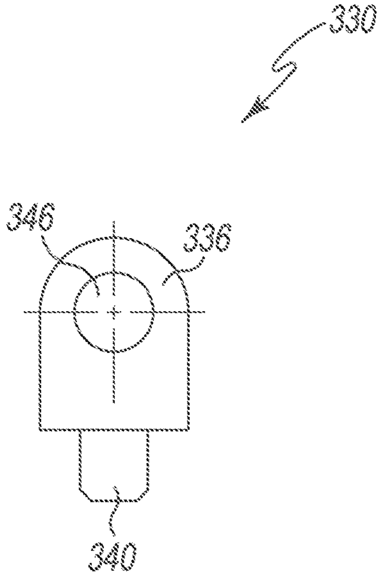

Referring now to FIGS. 18-20, in some embodiments, a surgical instrument adapter 330 may be assembled with the tibial template 178 and the pointer 150 in order to perform the UKA procedure. The adapter 330 includes an elongated body 332, which may be formed from a polymeric material such as polyphenylsulfone (PPSU). The adapter 330 may be molded, additively manufactured, or otherwise manufactured. In some embodiments, the adapter 330 may be formed from a metallic material.

The body 332 includes an outer surface 334 that extends from an end 336 to another end 338. A tab 340 is positioned along the body 332 and extends outward from the outer surface 334. The body 332 further includes an inner wall 342 that extends inwardly into the body 332 from an opening 344 defined in the end 336 to an end wall 346. The inner wall 342 and the end wall 346 cooperate to define a slot 348 that extends linearly from the end 336 toward the end 338.

In use, as part of the UKA procedure, the surgeon or other user assembles the surgical instrument adapter 330 with the tibial template 178 and the pointer 150. As shown in FIG. 18, to assemble the adapter 330 and the pointer 150, the tip 160 of the pointer 150 is inserted through the opening 344 into the slot 348 of the adapter 330. The pointer 150 is inserted until the tip 160 contacts the end wall 346, which retains the tip 160 of the pointer 150 at a predetermined position relative to the adapter 330 (within manufacturing tolerances). In some embodiments, the pointer 150 may be free to rotate relative to the adapter 330 while the tip 160 is held in the predetermined position relative to the adapter 330. To assemble the adapter 330 with the tibial template 178, the tab 340 of the adapter 330 is inserted into the keel slot 190 of the tibial template 178. When inserted, the outer wall of the tab 340 engages with the inner wall 188 of the keel slot 190.

After assembling the adapter 330 with the tibial template 178 and the pointer 150, the tibial template 178 may be placed onto the transverse cut surgically prepared surface 206 of the patient's tibia 164 as described above. Also as described above, the surgeon may use the system 10 to determine the appropriate anterior/posterior position for the tibial template 178. The surgeon may refer to a user interface 208 similar to that shown in FIGS. 14 and 15 in order to position the tibial template 178 according to a predetermined surgical plan.

Figure 21:
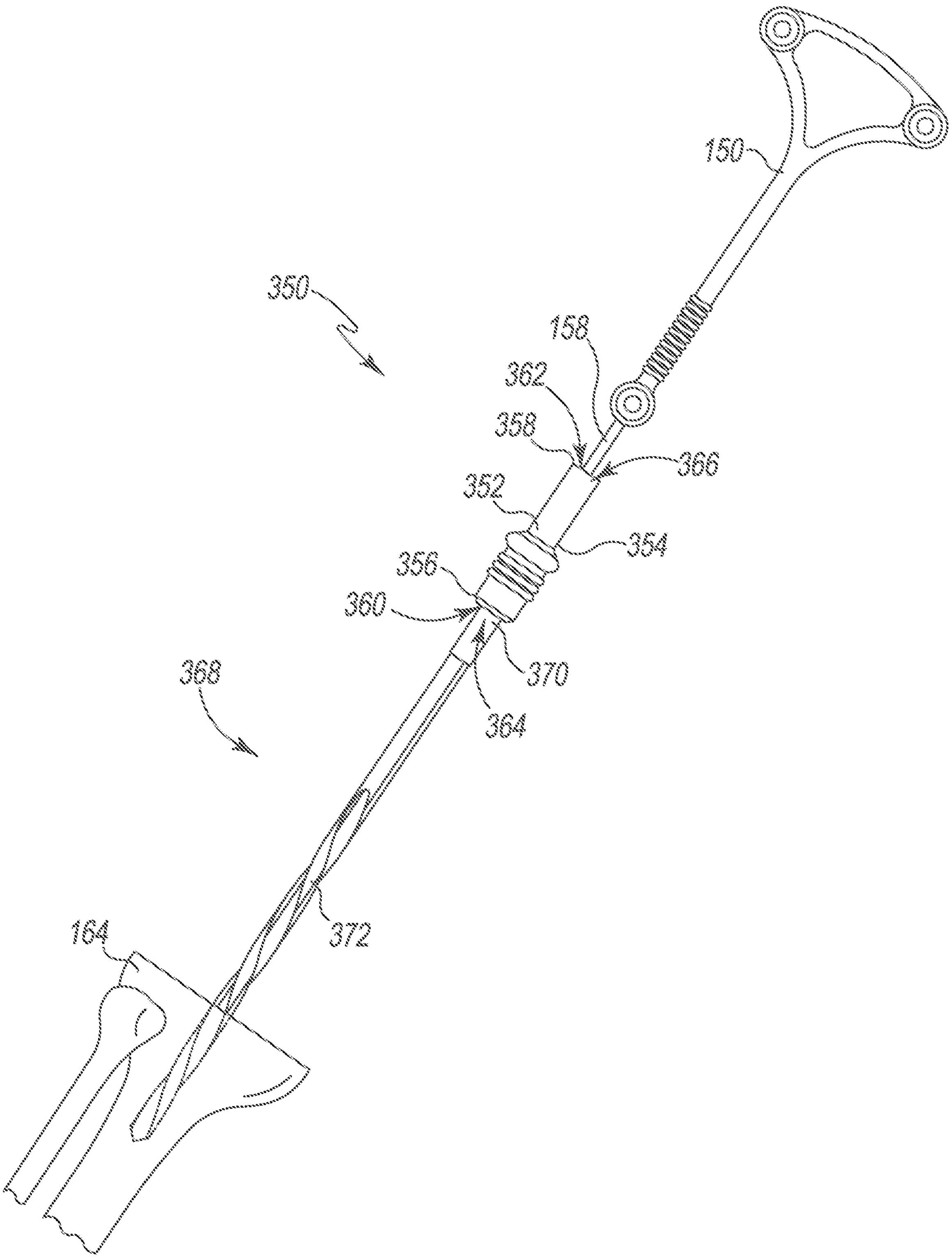
FIG. 21 is a perspective diagram of a surgical instrument assembly including another surgical instrument adapter, a surgical reamer, and the pointer registration tool in use during an orthopaedic surgical procedure.

Referring now to FIG. 21, another embodiment of a surgical instrument adapter 350 includes an elongated body 352, which may be formed from a polymeric material such as polyphenylsulfone (PPSU). The adapter 350 may be molded, additively manufactured, or otherwise manufactured. In some embodiments, the adapter 350 may be formed from a metallic material.

The body 352 includes a roughly cylindrical outer surface 354 that extends from an end 356 to another end 358. A circular opening 360, 362 is defined on each respective end 356, 358. An inner wall extends inward into the body 352 from each opening 360, 362 and each defines a respective slot 364, 366. The body 352 may include an inner end wall positioned between and separating the slots 364, 366. In some embodiments, the slots 364, 366 may be in communication, for example via a port defined in the inner end wall.

In use, the surgical instrument adapter 350 may be used with a surgical reamer 368 and the system 10 to perform a UKA orthopeadic surgical procedure or other surgical procedure. The surgical reamer 368 is an elongated surgical instrument that includes a shaft 370 positioned on an end and multiple cutting flutes 372 positioned on another end.

To assemble the adapter 350 and the pointer 150, the tip 160 of the pointer 150 is inserted through the opening 362 into the slot 366 of the adapter 350. The pointer 150 is inserted until the tip 160 contacts the end wall, which retains the tip 160 at a predetermined position relative to the adapter 350 (within manufacturing tolerances). In some embodiments, the pointer 150 may be free to rotate relative to the adapter 350 while the tip 160 of the pointer 150 is held in the predetermined position relative to the adapter 350. To assemble the adapter 250 with the reamer 368, the shaft 370 of the reamer 368 is inserted through the opening 360 into the slot 364 of the adapter 350. The reamer 368 is inserted until the shaft 370 contacts the end wall, which retains the tip 160 of the pointer 150 at a predetermined position relative to the reamer 368.

After assembling the adapter 350 with the reamer 368 and the pointer 150, the surgeon may insert the reamer 368 into the intramedullary canal of the patient's bone (e.g., the tibia 364 as shown in FIG. 21 or the femur). The system 10 may use the location of the pointer 150 to determine the reaming depth and/or angle of the reamer 368 relative to the patient's bone. The surgeon may refer to a user interface similar to those shown in FIGS. 7-8 and 14-15 in order to position the reamer 368 at a final reaming depth and/or angle according to a predetermined surgical plan.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method for performing an orthopaedic surgical procedure, the method comprising:

inserting a pointer end of a navigated pointer instrument into a slot defined in an adapter instrument such that the pointer end is held in a predetermined position relative to the adapter instrument, inserting a lug of the adapter instrument into a hole defined in a surgical guide instrument such that the adapter instrument is held in a predetermined position relative to the surgical guide instrument, positioning a first bone-contacting surface of the surgical guide instrument on a first surgically prepared surface of a patient's bone after inserting the pointer end of the navigated pointer instrument into the slot and inserting the lug into the hole, and determining a position of the surgical guide instrument relative to the patient's bone by sensing a position of the navigated pointer instrument using a surgical navigation system while the surgical guide instrument is positioned on the patient's bone.

2. The method of claim 1, wherein the pointer end is free to rotate relative to the adapter instrument while being held in the predetermined position relative to the adapter instrument.

3. The method of claim 1, wherein the surgical guide instrument comprises a femoral finishing block, and wherein the first surgically prepared surface of the patient's bone comprises a distal cut surface of a femur.

4. The method of claim 3, further comprising positioning a second bone-contacting surface of the surgical guide instrument on a posterior cut surface of the femur while the first bone-contacting surface of the surgical guide instrument is positioned on the distal cut surface of the femur.

5. The method of claim 1, wherein the surgical guide instrument comprises a tibial template and the first surgically prepared surface of the patient's bone comprises a transverse cut surface of a tibia.

6. The method of claim 5, further comprising positioning a second bone-contacting surface of the surgical guide instrument on a sagittal cut surface of the tibia while the first bone-contacting surface of the surgical guide instrument is positioned on the transverse cut surface of the tibia.

7. The method of claim 1, further comprising displaying, by the surgical navigation system, the position of the surgical guide instrument relative to the patient's bone.

8. The method of claim 7, further comprising displaying, by the surgical navigation system, an indication of a predetermined position for the surgical guide instrument relative to the position of the surgical guide instrument.

9. The method of claim 8, further comprising indicating, by the surgical navigation system, when the surgical guide instrument is positioned at the predetermined position for the surgical guide instrument.

10. The method of claim 1, wherein the adapter instrument comprises an elongated body extending from a first end to a second end, wherein the elongated body comprises (i) an end wall positioned at the first end of the elongated body and (ii) an inner wall extending inwardly from an opening defined in the second end of the elongated body to the end wall, and wherein the inner wall and the end wall define the slot that receives the pointer end of the navigated pointer instrument such that the pointer end is held in the predetermined position relative to the adapter instrument.

11. The method of claim 10, wherein the slot extends from the second end toward the first end, and wherein the lug extends from the first end in line with the slot.

12. The method of claim 10, wherein the lug comprises a cylindrical outer surface extending outward from the elongated body at the first end.

13. The method of claim 10, wherein the lug comprises a tapered outer surface extending outward from the elongated body at the first end.

14. The method of claim 10, wherein a port is defined in the end wall, the port having a width smaller than a width of the opening defined in the second end.

15. The method of claim 10, wherein the adapter instrument further comprises a flange extending from the first end to the second end, and wherein the lug extends outward from the flange transverse to the slot that receives the pointer end of the navigated pointer instrument.

16. The method of claim 15, wherein the adapter instrument further comprises a second lug extending outward from the flange transverse to the slot that receives the pointer end of the navigated pointer instrument.

17. The method of claim 15, wherein the lug comprises a rectangular tab that extends outward from the flange and is sized to be received in a keel slot defined in the surgical guide instrument.

* * * * *